United States Patent [19]

Gribble et al.

[11] Patent Number: 4,668,671

[45] Date of Patent: May 26, 1987

[54] TRICYCLIC DERIVATIVES AND PHARMACEUTICAL USE

[75] Inventors: Andrew D. Gribble, Knebworth; Robert J. Ife, Stevenage, both of England

[73] Assignee: Smith Kline & French Laboratories Limited, Welwyn Garden City, England

[21] Appl. No.: 854,951

[22] Filed: Apr. 23, 1986

[30] Foreign Application Priority Data

Apr. 26, 1985 [GB] United Kingdom ............... 8510680

[51] Int. Cl.$^4$ ................ A61K 31/535; A61K 31/54; C07D 265/38; C07D 279/24
[52] U.S. Cl. .................................... 514/211; 514/215; 514/217; 514/223; 514/230; 514/250; 514/292; 514/293; 514/297; 540/548; 540/550; 540/577; 540/578; 540/592; 544/34; 544/43; 544/101; 544/104; 544/345; 544/347; 546/81; 546/83; 546/104

[58] Field of Search ............... 544/34, 43, 101, 104, 544/345, 347; 546/81, 83, 104; 540/548, 550, 577, 578, 592; 514/215, 217, 211, 223, 230, 250, 292, 293, 297

[56] References Cited

U.S. PATENT DOCUMENTS

| 2,837,518 | 6/1958 | Jacob et al. | 260/243 |
| 2,945,855 | 7/1960 | Feldkamp et al. | 260/243 |
| 2,974,139 | 3/1961 | Schuler et al. | 260/243 |

FOREIGN PATENT DOCUMENTS

| 1034638 | 12/1958 | Fed. Rep. of Germany . |
| 2009555 | 10/1970 | Fed. Rep. of Germany . |
| 814512 | 6/1959 | United Kingdom . |
| 861420 | 2/1961 | United Kingdom . |
| 861807 | 3/1961 | United Kingdom . |

Primary Examiner—Richard L. Raymond
Attorney, Agent, or Firm—Linda E. Hall; Stuart R. Suter; Alan D. Lourie

[57] ABSTRACT

This invention describes tricyclic derivatives which are useful as histamine $H_1$-antagonists. A particular compound of this invention is 3-[3-(pyrido[3,2-b][1,4]-benzothiazin-10-yl)propylamino]-4-(pyrid-4-ylmethylamino)-1,2,5-thiadiazole-1-oxide.

17 Claims, No Drawings

TRICYCLIC DERIVATIVES AND PHARMACEUTICAL USE

This invention relates to certain tricyclic derivatives, pharmaceutical compositions containing them and a method of blocking histamine $H_1$-receptors by administering them.

Histamine, a physiologically active compound endogenous in mammals, exerts its action by interacting with certain sites called receptors. One type of receptor is known as a histamine $H_1$-receptor (Ash and Schild, Brit. J. Pharmac, 1966, 27, 427) and the actions of histamine at these receptors are inhibited by drugs commonly called "antihistamines" (histamine $H_1$-antagonists) a common example of which is mepyramine.

According to the present invention there is provided compounds of formula (1):

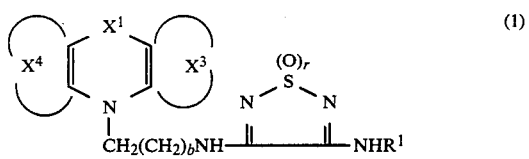

and pharmaceutically acceptable salts thereof, where
$X^1$ is oxygen, sulphur; $-NR^2-$ (where $R^2$ is hydrogen, $C_{1-6}$alkyl or $C_{1-6}$alkanoyl); $-CHR^3-$; $-CH_2CHR^3-$; $-O-CHR^3-$; or $-S-CHR^3-$ (where $R^3$ is hydrogen or $C_{1-6}$alkyl);

$X^3$ and $X^4$ are the same or different and represent a fused benzo or pyrido ring, each ring being optionally substituted with $C_{1-6}$alkyl, $C_{1-6}$alkoxy or halogen;

b is from 2 to 5;
r is 1 or 2; and
$R^1$ is hydrogen, $C_{1-6}$alkyl or a group $-CH_2R^5$ and $R^5$ is pyridyl optionally bearing one or two substituents which are the same or different and are $C_{1-6}$alkyl, $C_{1-6}$alkoxy, halogen or hydroxy;
or is phenyl or pyridyl bearing a carboxy, carboxamido, sulphonamido or hydroxy-$C_{1-6}$alkyl group and optionally bearing a $C_{1-6}$alkyl, $C_{1-6}$alkoxy, hydroxy or halogen substituent;
or is N-oxo-pyridyl optionally bearing a $C_{1-6}$alkyl, $C_{1-6}$alkoxy, or halogen substituent.

Referring to $X^1$, examples of $C_{1-6}$alkyl groups for $R^2$ and $R^3$ are methyl, ethyl, n-propyl, iso-propyl, n-butyl and t-butyl. A preferable $C_{1-6}$alkyl group is methyl.

Examples of $C_{1-6}$alkanoyl groups for $R^2$ are acetyl, n-propanoyl, n-butanoyl and n-pentanoyl. A preferable $C_{1-6}$alkanoyl group is acetyl.

Preferably $R^2$ and $R^3$ are hydrogen.

Preferably $X^1$ is sulphur or $-CH_2-CHR^3-$ where $R^3$ is hydrogen. Most preferably $X^1$ is sulphur.

Referring to $X^3$ and $X^4$, examples of $C_{1-6}$alkyl substituents are methyl, ethyl, n-propyl, iso-propyl, n-butyl and t-butyl.

Examples of $C_{1-6}$alkoxy substituents are methoxy, ethoxy, n-propoxy and n-butoxy.

Examples of halogen substituents are fluoro, chloro and bromo.

Where $X^3$ or $X^4$ is pyrido, it can be pyrido[2,3]-, pyrido[3,4]-, pyrido[4,3]- or pyrido[3,2]- relative to the nitrogen atom.

Preferably $X^3$ is pyrido, particularly pyrido[2,3]- relative to the nitrogen atom or benzo.

Preferably $X^4$ is benzo.

Preferably when $X^3$ and $X^4$ together have two substituents, one substituent is in each ring.

Preferably $X^3$ and $X^4$ are unsubstituted.

By way of example b can be 2 or 3. Preferably it is 2.

Examples of $C_{1-6}$alkyl groups for $R^1$ are methyl, ethyl and n-propyl.

Preferably $R^1$ is hydrogen or a group $-CH_2R^5$.

A further class of compounds falling within the scope of this invention is where $R^5$ is pyridyl optionally bearing one or two substituents which are the same or different and are $C_{1-6}$alkyl, $C_{1-6}$alkoxy, halogen or hydroxy. A particular example is pyrid-4-yl.

A further class of compounds within the scope of this invention is where $R^5$ is phenyl or pyridyl bearing a carboxy, carboxamido, sulphonamido or hydroxy-$C_{1-6}$alkyl group and optionally bearing a $C_{1-6}$alkyl, $C_{1-6}$alkoxy, hydroxy or halogen substituent.

Examples of hydroxy-$C_{1-6}$alkyl groups are hydroxymethyl and hydroxyethyl.

Examples of particular values for $R^5$ when it is a substituted phenyl group are 2-methyl-4-carboxyphenyl, 2-methoxy-4-carboxyphenyl, 2-chloro-4-carboxyphenyl, 3-methyl-4-carboxamidophenyl, 3-methoxy-4-carboxamidophenyl, 3-chloro-4-carboxamidophenyl, 3-fluoro-4-carboxamidophenyl, 2-methyl-4-sulphonamidophenyl, 2-methoxy-4-sulphonamidophenyl, 2-chloro-4-sulphonamidophenyl, 4-carboxyphenyl, 4-carboxamidophenyl and 4-sulphonamidophenyl.

Where $R^5$ is a substituted pyridyl group, preferably it is a 6-substituted pyrid-4-yl group.

Examples of particular values for $R^5$ when it is a substituted pyridyl group are 2-methyl-6-carboxypyrid-3-yl, 2-methoxy-6-carboxypyrid-3-yl, 2-chloro-6-carboxypyrid-3-yl, 5-methyl-6-carboxamidopyrid-3-yl, 5-methoxy-6-carboxamidopyrid-3-yl, 5-chloro-6-carboxamidopyrid-3-yl, 5-fluoro-6-carboxamidopyrid-3-yl, 2-methyl-6-sulphonamidopyrid-3-yl, 2-methoxy-6-sulphonamidopyrid-3-yl, 2-chloro-6-sulphonamidopyrid-3-yl, 6-carboxypyrid-3-yl, 6-carboxamidopyrid-3-yl and 6-sulphonamidopyrid-3-yl.

A further class of compounds within the scope of this invention is where $R^5$ is N-oxo-pyridyl optionally bearing a $C_{1-6}$alkyl, $C_{1-6}$alkoxy or halogen substituent.

Preferably the group $-CH_2-$ is attached at position 4 of the pyridyl group.

Examples of particular values for $R^5$ in compounds of this class are 6-methyl-N-oxo-pyrid-4-yl, 6-methoxy-N-oxo-pyrid-4-yl, 6-chloro-N-oxo-pyrid-4-yl and especially N-oxo-pyrid-4-yl.

Preferably $R^5$ is pyrid-4-yl or N-oxo-pyrid-4-yl.

Preferably r is 1.

Compounds of formula (1) form pharmaceutically acceptable salts with pharmaceutically acceptable acid addition salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

Particular compounds falling within the scope of this invention are:
3-[3-(pyrido[3,2-b][1,4]benzothiazin-10-yl)-propylamino]-4-amino-1,2,5-thiadiazole-1-oxide
3-[3-(pyrido[3,2-b][1,4]-benzothiazin-10-yl)propylamino]-4-(pyrid-4-ylmethylamino)-1,2,5-thiadiazole-1-oxide 3-[3-(N-phenothiazinyl)propylamino]-4-amino-1,2,5-thiadiazole-1-oxide 3-[3-(N-phenothiazinyl)propylamino]-4-(pyrid-4-yl-methylamino)-1,2,5-thiadiazole-1-oxide 3-[3-(10,11-dihydro-5H-dibenz[b,f]azepin-5-yl)propylamino]-4-amino-1,2,5-thiadiazole-1-oxide and there pharmaceutically acceptable salts.

The compounds of formula (1) can be prepared by reacting a compound of formula (5):

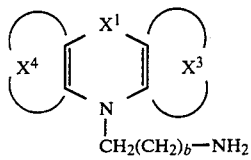   (5)

where b, $X^1$, $X^3$ and $X^4$ are as defined with reference to formula (1) with a compound of formula (6):

   (6)

where r is 1 or 2 and $X^8$ is a group displaceable with an amine and $X^9$ is a group displaceable with an amine or a group of formula —$NHR^1$ where $R^1$ is as defined with reference to formula (1) and where $X^9$ is a group displaceable with amine, reacting with an amine of formula (7):

$R^1NH_2$   (7)

and thereafter optionally converting the compound of formula (1) so obtained into a salt.

Examples of leaving groups displaceable by amines are where $X^8$ and $X^9$ are QS—, QSO—, QSO$_2$—, or QO— (Q being $C_{1-6}$alkyl, aryl or aralkyl) halogen, particularly chlorine and bromine, and nitroamino. Preferably the groups $X^8$ and $X^9$ are QO— where Q is methyl.

The conditions under which the reaction is carried out depends upon the nature of the reagents. For example the reaction is generally carried out at moderate to low temperature, e.g. from 0° C. to room temperature. The choice of solvent is affected by the solubility characteristics of the reagents. Preferably the solvent is pyridine, a picoline or mixture of picolines, a $C_{1-6}$alkanol, preferably ethanol or 1-propanol, 1,2-ethanediol, a high boiling alkoxyaryl ether for example anisole, or a polar aprotic solvent, for example dimethylformamide, diethylacetamide, dimethylsulphoxide, hexamethylphosphoramide or sulpholane.

Pharmaceutically acceptable salts of compounds of formula (1) can be prepared by standard methods, for example by reacting a solution of the compound of formula (1) with a solution of the acid.

Compounds of formula (5) are also included in this invention. These compounds can be prepared by reacting a compound of formula (8):

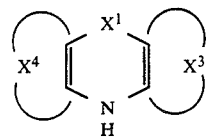   (8)

where $X^1$, $X^3$ and $X^4$ are as defined with reference to formula (1), with a compound of formula (9):

$Y(CH_2)_{b+1}R^6$   (9)

where Y is halogen and $R^6$ is a protected amino group and b is as defined with reference to formula (1) in the presence of a strong base and thereafter removing any protecting groups.

Examples of strong bases are alkali metal hydrides (particularly sodium hydride) alkali metal amides (particularly sodamide) and alkyl alkali metals for example butyl lithium.

The reaction is carried out in the presence of a non-interfering solvent, that is to say one which is substantially inert to the reagents and products. The choice of any particular solvent depends upon the nature of the base. For example, for an alkali metal hydride preferably the solvent is dimethylsulphoxide. For alkali metal amides, preferably the solvent is liquid ammonia. For alkyl alkali metals, preferably the solvent is an ether, for example dimethylether or tetrahydrofuran.

The reaction is carried out at moderate to low temperatures depending upon the base and solvent. For example, where the base is an alkali metal hydride in dimethylsulphoxide the reaction is carried out at room temperature. Where the base is an alkali metal amide in ammonia, the reaction is carried out below the boiling point of liquid ammonia. Where the base is an alkyl alkali metal, the reaction can be carried out from room temperature to $-78°$ C. and preferably in an inert atmosphere.

Examples of protected amino groups for $R^6$ include phthalimido and where the base is an alkali metal amide it can be an acid addition salt for example the hydrochloride. In formula (9) Y can be chlorine, bromine or iodine.

The protected amino group can be converted into amino by standard methods, for example when it is phthalimido by reaction with hydrazine.

Compounds of formulae (7) to (9) are known or can be made by analogy with known methods.

Compounds of formula (6) are known or can be made by analogy with known methods as described in U.S. Pat. No. 4,062,863 and U.K patent application No. 2,067,987A.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of Examples 1–5 have $pA_2$ values greater than 7.

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artifically with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Topical formulations for administration to the eye include solutions and ointments. Solutions for administration to the eye comprise the active compound and a sterile aqueous carrier for example an isotonic buffer particularly a buffered solution of boric acid, sodium chloride or sodium borate. The buffer can be a conventional phosphate buffer which maintains the pH of the solution in a physiological pH range. An example of such a buffer is Sorensen's buffer. For an ointment the carrier can be petrolatum.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier or parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol so that the patient may administer to himself a single dose.

Where appropriate, small amounts of bronchodilators and anti-asthmatics for example sympathomimetic amines particularly isoprenaline, isoetharine, salbutamol, phenylephrine and ephedrine, xanthine derivatives particularly theophylline and aminophylline; and corticosteroids particularly prednisolone and adrenal stimulants particularly ACTH can be included. As in common practice, the compositions will usually be accompanied by written or printed directions for use in the medical treatment concerned, in this case as a histamine $H_1$-antagonist for treatment of, for example, asthma, hayfever, rhinitis or allergic eczema.

Each dosage unit for oral administration contains preferably from 5 to 200 mg of a compound of formula (1) or a pharmaceutically acceptable salt thereof calculated as the free base.

The invention also includes a method of blocking histamine $H_1$-receptors which comprises administering to an animal an effective amount to block said receptors of a compound of formula (1) or a pharmaceutically acceptable salt thereof.

The compounds of the invention will normally be administered to a subject for the treatment of rhinitis, hayfever, bronchial asthma or allergic eczema. An adult patient will receive an oral dose of between 15 mg and 400 mg and preferably between 15 mg and 200 mg or an intravenous, subcutaneous or intramuscular dose of between 1 mg and 50 mg, and prefeably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

(i) To 50% sodium hydride (1.45 g) washed with petroleum ether, was added dimethylsulphoxide (DMSO) (20 ml) and the mixture heated to 70° C. until hydrogen evolution ceased. After cooling, a solution of 10H-pyrido-[3,2-b]-[1,4]benzothiazine (5.51 g) in DMSO (20 ml) was added. After 5 min., a solution of 3-bromopropylphthalimide (8.11 g) in DMSO (20 ml)

was added dropwise, maintaining the temperature between 25°–35° C. After 2 hr., the mixture was diluted with water (200 ml), extracted with chloroform (3×80 ml), and the extracts washed with water (1×100 ml) and dried ($K_2CO_3$). Concentration in vacuo afforded an oil which was chromatographed (silica, $CHCl_3$) to afford 4.73 g (44%) of phthalimido intermediate. This was refluxed in ethanol (ca. 100 ml) with hydrazine hydrate (2.43 ml) for 2–3 hr. On cooling, the precipitated solid was removed by filtration, the filtrate evaporated, and taken up in 2N HCl (50 ml). Solid was filtered off, and the filtrate basified to pH 14. Extraction with $CHCl_3$ and concentration gave 3-(pyrido[3,2-b][1,4]-benzothiazin-10-yl)-propylamine (2.6 g, 8.3%) as an oil which was used without further purification.

(ii) 3-(Pyrido[3,2-b][1,4]-benzothiazin-10-yl)propylamine (1.5 g) in methanol (20 ml) was added dropwise to a solution of 3,4-dimethoxy-1,2,5-thiadiazole-1-oxide (0.95 g) in methanol (35 ml) at 0°–5° C. After 2 hr. at 0°–10° C., a solution of methanol saturated with ammonia (10 ml) was added and the mixture allowed to stand overnight at room temperature. The solvent was evaporated and the residue, after recrystallisation from dimethylformamide/ethanol, chromatographed (silica gel, chloroform/methanol 10:1) to give, after crystallisation from acetone, 3-[3-(pyrido[3,2-b][1,4]benzothiazin-10-yl)propylamino]-4-amino-1,2,5-thiadiazole-1-oxide (0.3 g, 14%) m.p. 225°–7° C.

$C_{16}H_{15}N_6OS_2.0.1CHCl_3$: Found: C 50.43; H 4.35; N 21.76; S 16.42. Requires: C 50.30; H 4.22; N 21.86; S 16.68.

EXAMPLE 2

3-(Pyrido[3,2-b][1,4]-benzothiazin-10-yl)propylamine (1.62 g) in methanol (20 ml) was added dropwise to a solution of 3,4-dimethoxy-1,2,5-thiadiazole-1-oxide (1.02 g) in methanol (40 ml) at 0°–5° C. After 2 hr. at room temperature, 4-aminomethylpyridine (1.02 g) in methanol (10 ml) was added and allowed to stand for 3 days at room temperature. More 4-aminomethylpyridine (1.02 g) and chloroform (30 ml) were added and this was allowed to stand for 4 days. The solvent was evaporated and the residue chromatographed under medium pressure (silica gel, chloroform/methanol 19:1) to give, after crystallisation from ethanol, 3-[3-(pyrido[3,2-b][1,4]-benzothiazin-10-yl)propylamino]-4-(pyrid-4-ylmethylamino)-1,2,5-thiadiazole-1-oxide (1.49 g, 51%) m.p. 189°–190° C.

$C_{22}H_{21}N_7OS_2.0.1C_2H_5OH$: Found: C 57.12; H 4.72; N 20.95. Requires: C 56.95; H 4.65; N 20.94.

EXAMPLE 3

(i) Substituting phenothiazine (16.49 g) for 10H-pyrido-[3,2-b]-[1,4]benzothiazine, and using corresponding molar proportions of other reagents in the method of Example 1(i), gave 3-(N-phenothiazinyl)-propylamine (4.89 g, 22%) as an oil which was used without further purification.

(ii) 3-(N-Phenothiazinyl)propylamine (1.38 g) in methanol (10 ml) was added dropwise to a solution of 3,4-dimethoxy-1,2,5-thiadiazole-1-oxide (0.87 g) in methanol (30 ml) at 0°–5° C. After 2 hr. at room temperature, ammonia was slowly bubbled through the stirred solution for 1 hr. at 0.5° C., and then left at room temperature overnight. The solvent was evaporated and the residue chromatographed (silica gel, chloroform/methanol 24:1) to give, after crystallisation from ethanol, 3-[3-(N-phenothiazinyl)propylamino]-4-amino-1,2,5-thiadiazole-1-oxide (0.79 g, 40%), m.p. 214°–216° C.

$C_{17}H_{17}N_5OS_2$: Found: C 54.96; H 4.61; N 18.85; S 17.26. Requires: C 54.82; H 4.70; N 18.50; S 16.99.

EXAMPLE 4

3-(N-Phenothiazinyl)propylamine (1.1 g) in methanol (10 ml) was added dropwise to a solution of 3,4-dimethoxy-1,2,5-thiadiazole-1-oxide (0.7 g) in methanol (30 ml) at 0°–5° C. After 2 hr. at room temperature, a solution of 4-aminomethylpyridine (0.7 g) in methanol (5 ml) was added at 0°–5° C. and the solution allowed to stand at room temperature for 20 hr. The solvent was evaporated and the residue chromatographed (silica gel, chloroform/methanol 97:3) to give, after crystallization from ethanol, 3-[3-(N-phenothiazinyl)propylamino]-4-(pyrid-4-ylmethylamino)-1,2,5-thiadiazole-1-oxide (0.55 g, 28%), m.p. 178°–180° C.

$C_{23}H_{22}N_6OS_2$: Found: C 59.71; H 4.79; N 18.17; S 13.86. Requires: C 59.88; H 4.89; N 17.99; S 13.72.

EXAMPLE 5

(i) A mixture of sodamide (1.99 g) and 10,11-dihydro-5H-dibenz[b,f]azepine (10 g) in xylene (120 ml) was heated under reflux for 3 hr. A solution of 3-bromopropylphthalimide (13.67 g) in xylene (30 ml) was added at 35° C., and the mixture heated under reflux for 20 hr. Filtration and concentration afforded an oil (21.7 g) which was heated under reflux with hydrazine hydrate (6.95 ml) in ethanol (300 ml) for 3 hr. The reaction mixture was filtered, the filtrate was evaporated to afford a residue which was taken up in ethyl acetate (400 ml) and the resultant mixture filtered. The filtrate was extracted with 2N HCl (4×200 ml), the pH adjusted to 14 and then extracted with ether. Concentration afforded 3-(10,11-dihydro-5H-dibenz[b,f]azepin-5-yl)propylamine (2.25 g, 18%) as an oil which was used without further purification.

(ii) Substituting 3-(10,11-dihydro-5H-dibenz[b,f]azepin-5-yl)propylamine (1.2 g) for 3-(N-phenothiazinyl)-propylamine and using corresponding molar proportions of other reagents in the method of Example 3(ii) gave 3-[3-(10,11-dihydro-5H-dibenz[b,f]azepin-5-yl)propylamino]-4-amino-1,2,5-thiadiazole-1-oxide (0.36 g, 21%), m.p. 227°–30° C.

$C_{19}H_{21}N_5OS$:
Found: C 61.73 H 5.71 N 18.99 S 8.47. Requires: C 62.10 H 5.76 N 19.06 S 8.72.

EXAMPLE 6

A pharmaceutical composition for oral administration is prepared containing

|   |   | % by weight |
|---|---|---|
| A | 3-[3-(pyrido[3,2-b][1,4]-benzo-thiazin-10-yl)propylamino]-4-(pyrid-4-ylmethylamino)-1,2,5-thiadiazole-1-oxide | 55 |
|   | Dibasic calcium phosphate dihydrate | 20 |
|   | Approved coloring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellulose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

EXAMPLE 7

A pharmaceutical composition for injectable administration is prepared by forming a solution of 3-[3-(pyrido[3,2-b][1,4]benzothiazin-10-yl)propylamino]-4-(pyrid-4-ylmethylamino)-1,2,5-thiadiazole-1-oxide hydrochloride salt in sterile water to give a 1 to 5% w/w solution. The solution was clarified by filtration and filled into vials which are sealed and sterilised. A suitable vial contains 2 ml of the solution.

What is claimed is:

1. A compound of formula (1):

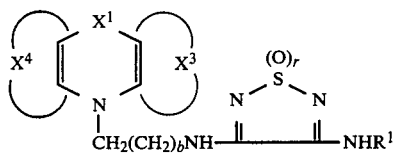

(1)

or a pharmaceutically acceptable salt thereof, where
$X^1$ is oxygen; sulphur; —$NR^2$— (where $R^2$ is hydrogen, $C_{1-6}$alkyl or $C_{1-6}$alkanoyl); —$CHR^3$—; —$CH_2CHR^3$—; —O—$CHR^3$—; or —S—$CHR^3$— (where $R^3$ is hydrogen or $C_{1-6}$alkyl);
$X^3$ and $X^4$ are the same or different and represent a fused benzo or pyrido ring, each ring being optionally substituted with $C_{1-6}$alkyl, $C_{1-6}$alkoxy or halogen;
b is from 2 to 5;
r is 1 or 2; and
$R^1$ is hydrogen, $C_{1-6}$alkyl or a group —$CH_2R^5$ and $R^5$ is pyridyl optionally bearing one or two substituents which are the same or different and are $C_{1-6}$alkyl, $C_{1-6}$alkoxy, halogen or hydroxy;
or is phenyl or pyridyl bearing a carboxy, carboxamido, sulphonamido or hydroxy-$C_{1-6}$alkyl group and optionally bearing a $C_{1-6}$alkyl, $C_{1-6}$alkoxy, hydroxy or halogen substituent;
or is N-oxo-pyridyl optionally bearing a $C_{1-6}$alkyl, $C_{1-6}$alkoxy, or halogen substituent.

2. A compound as claimed in claim 1 where $X^1$ is sulphur or —$CH_2$—$CHR^3$— where $R^3$ is hydrogen.

3. A compound as claimed in claim 2 where $X^1$ is sulphur.

4. A compound as claimed in claim 1 where $X^3$ and $X^4$ are unsubstituted.

5. A compound as claimed in claim 1 wherein $X^3$ is pyrido[2,3]- relative to the nitrogen atom.

6. A compound as claimed in claim 1 where $X^4$ is benzo.

7. A compound as claimed in claim 1 where b is 2.

8. A compound as claimed in claim 1 where $R^1$ is hydrogen or —$CH_2R^5$.

9. A compound as claimed in claim 1 where $R^5$ is pyrid-4-yl or N-oxo-pyrid-4-yl.

10. A compound as claimed in claim 1 where r is 1.

11. A compound of claim 1, said compound being 3-[3-(pyrido[3,2-b][1,4]benzothiazin-10-yl)-propylamino]-4-amino-1,2,5-thiadiazole-1-oxide, or a pharmaceutically acceptable acid addition salt thereof.

12. A compound of claim 1, said compound being 3-[3-(pyrido[3,2-b][1,4]-benzothiazin-10-yl)propylamino]-4-(pyrid-4-ylmethylamino)-1,2,5-thiadiazole-1-oxide, or a pharmaceutically acceptable acid addition salt thereof.

13. A compound of claim 1, said compound being 3-[3-(N-phenothiazinyl)propylamino]-4-amino-1,2,5-thiadiazole-1-oxide, or a pharmaceutically acceptable acid addition salt thereof.

14. A compound of claim 1, said compound being 3-[3-(N-phenothiazinyl)propylamino]-4-(pyrid-4-ylmethylamino)-1,2,5-thiadiazole-1-oxide, or a pharmaceutically acceptable acid addition salt thereof.

15. A compound of claim 1, said compound being 3-[3-(10,11-dihydro-5H-dibenz[b,f]azepin-5-yl)propylamino]-4-amino-1,2,5-thiadiazole-1-oxide, or a pharmaceutically acceptable acid addition salt thereof.

16. A pharmaceutical composition having histamine $H_1$-antagonist activity comprising a compound as claimed in claim 1 and a pharmaceutically acceptable carrier.

17. A method of blocking histamine $H_1$-receptors which comprises administering to an animal an effective amount to block said receptors of a compound according to claim 1 or a pharmaceutically acceptable salt thereof.

* * * * *